(12) United States Patent
Seelam et al.

(10) Patent No.: US 10,987,269 B2
(45) Date of Patent: Apr. 27, 2021

(54) SYSTEMS AND METHODS FOR CONTROLLING LIGHT IN AN INCUBATOR

(71) Applicant: Kilo Medical Solutions, LLC, Richmond, VA (US)

(72) Inventors: Joshnamaithili Seelam, Richmond, VA (US); Aniket Kulkarni, Glen Allen, VA (US); Kashyap Venuthurupalli, Ashburn, VA (US); Chandana Muktipaty, Glen Allen, VA (US)

(73) Assignee: Kilo Medical Solutions, LLC, Richmond, VA (US)

( * ) Notice: Subject to any disclaimer, the term of this patent is extended or adjusted under 35 U.S.C. 154(b) by 0 days.

(21) Appl. No.: 16/270,407

(22) Filed: Feb. 7, 2019

(65) Prior Publication Data
US 2019/0240098 A1 Aug. 8, 2019

Related U.S. Application Data

(60) Provisional application No. 62/627,444, filed on Feb. 7, 2018.

(51) Int. Cl.
*A61G 11/00* (2006.01)
*G02F 1/00* (2006.01)
(Continued)

(52) U.S. Cl.
CPC ............... *A61G 11/00* (2013.01); *G02F 1/00* (2013.01); *A61B 2503/045* (2013.01);
(Continued)

(58) Field of Classification Search
CPC ............... A61G 2203/30; A61G 11/00; A61G 2203/46; G02F 1/0121; G02F 1/13318
See application file for complete search history.

(56) References Cited

U.S. PATENT DOCUMENTS

D359,559 S 6/1995 Hawkins
5,566,413 A 10/1996 Webb et al.
(Continued)

FOREIGN PATENT DOCUMENTS

WO WO-2014124592 A1 * 8/2014 ............... B60J 3/04
WO 2016149527 A1 9/2016

OTHER PUBLICATIONS

Samuel Vásquez-Ruiz et al., "A light/dark cycle in the NICU accelerates body weight gain and shortens time to discharge in preterm infants", Early Human Development 90 (2014), pp. 535-540.
(Continued)

*Primary Examiner* — Kaylee R Wilson
(74) *Attorney, Agent, or Firm* — Nixon Peabody LLP; Thomas P. Pavelko

(57) ABSTRACT

The present disclosure provides for an incubator, which includes a film with a plurality of configurations. The configurations can include a first configuration to block the transmission of light through the film and a second configuration to be transparent to the transmission of light. The film can further allow any number of additional configurations with varying degrees of opacity, each opacity being between the opacities of the first and second configurations. The film can automatically change opacities based on input from an incubator processor or external devices configured to communicate with the incubator processor.

20 Claims, 6 Drawing Sheets

(51) Int. Cl.
*F21V 7/00* (2006.01)
*F21W 131/208* (2006.01)

(52) U.S. Cl.
CPC ........ *A61G 2203/46* (2013.01); *F21V 7/0008* (2013.01); *F21W 2131/208* (2013.01)

(56) References Cited

U.S. PATENT DOCUMENTS

| | | | |
|---|---|---|---|
| 9,433,524 B2 | 9/2016 | Nadeau | |
| 9,433,549 B2 | 9/2016 | Willemsen et al. | |
| 10,843,535 B1* | 11/2020 | Mazuir | G02F 1/13725 |
| 2001/0037049 A1* | 11/2001 | Salmon | A61G 11/00 600/22 |
| 2002/0173696 A1* | 11/2002 | Kolarovic | A61G 11/00 600/22 |
| 2003/0055310 A1 | 3/2003 | Salmon et al. | |
| 2004/0012762 A1* | 1/2004 | Faris | A61F 9/065 353/122 |
| 2015/0073204 A1 | 3/2015 | Rapoport | |
| 2017/0182282 A1 | 6/2017 | Rea et al. | |
| 2017/0231058 A1* | 8/2017 | Sadwick | H05B 33/0857 |
| 2017/0301288 A1 | 10/2017 | Perdices-Gonzalez et al. | |
| 2018/0182314 A1* | 6/2018 | Staton | A61G 11/00 |

OTHER PUBLICATIONS

Neonatal Intensive Care for Law Birth-weight Infants: Costs and Effectiveness (Health Technology Case Study 38), OTA-HCS-38, (Washington, DC; U.S. Congress, Office of Technology Assessment, Dec. 1987), Chapter 4 Financing Neonatal Intensive Care.
Roberto G. Rodriguez, Ph. D., et al., "Neonatal intensive care unit lighting: update and recommendations", Arch Argent Pediatr 2016;114(4), pp. 361-367.
Philip Lewis et al., "Perinatal Light Imprinting of Circadian Clocks and Systems (PLICCS): The PLICCS and Cancer Hypothesis", Frontiers in Oncology, Mar. 2017, vol. 7, Article 44, pp. 1-5.
Ryan W. Logan et al., "Rhythms of life: circadian disruption and brain disorders across the lifespan", Nature Reviews, vol. 20, Jan. 2019, pp. 49-65.
Stanley N. Graven, MD, et al., "Sleep and Brain Development, The Critical Role of Sleep in Fetal and Early Neonatal Brain Development", vol. 8, No. 4, pp. 174-179, Dec. 2008.
Daphna Yasova Barbeau, et al., "Sleep Disturbances in Newborns", Children, 2017, vol. 4, No. 90, pp. 1-16.
Special Care Nursery Admissions, March of Dimes, Source: National Perinatal Information System/Quality Analytic Prepared by March of Dimes Perinatal Data Center, 2011, pp. 1-3.
Serdar Cömert, MD, et al., "The Cost Analysis of Preterm Infants from a NICU of a State Hospital in Istanbul", Iran J. Pediatr, Jun. 2012, vol. 22, No. 2, pp. 185-190.
Debra H. Brandon, et al., "Timing for the Introduction of Cycled Light for Extremely Preterm Infants: A Randomized Controlled Trial", Res Nurs Health, Aug. 2017, vol. 40, No. 4, pp. 1-28.
Aditya Joshi, MD, et al., "Web Camera Use in the Neonatal Intensive Care Unit: Impact on Nursing Workflow", Clinical Medicine & Research, vol. 14, No. 1, pp. 1-6, Mar. 2016.
Ohlsson A. Morag, et al., "Cycled light in the intensive care unit for preterm and low birth weight infants (Review)", Cochrane Database of Systematic Reviews, 2011, Issue 1 Art No. CD006982.
Ohisson A. Morag, et al., Cycled light in the intensive care unit for preterm and low birth weight infants (Review), Cochrane Database of Systematic Reviews, 2013, Issue 8, Art No. CD006982.
Ohisson A. Morag, et al., Cycled light in the intensive care unit for preterm and low birth weight infants (Review), Cochrane Database of Systematic Reviews, 2016, Issue 8, Art No. CD006982.
International Search Report for PCT/US2019/017087 dated Apr. 8, 2019.
Written Opinion for PCTUS2019/017087 dated Apr. 8, 2019.
PCT International Preliminary Report on Patentability in International Application No. PCT/US2019/017087, dated Aug. 20, 2020.
Vernier, Vernier Surface Temperature Sensor, https://www.vernier.com/product/surface-temperature-sensor/, downloaded Aug. 25, 2020, USA.
Pasco, Pasport Skin/Surface Temperature Probe, https://www.pasco.com/products/sensors/temperature/ps-2131, downloaded Aug. 25, 2020, USA.

* cited by examiner

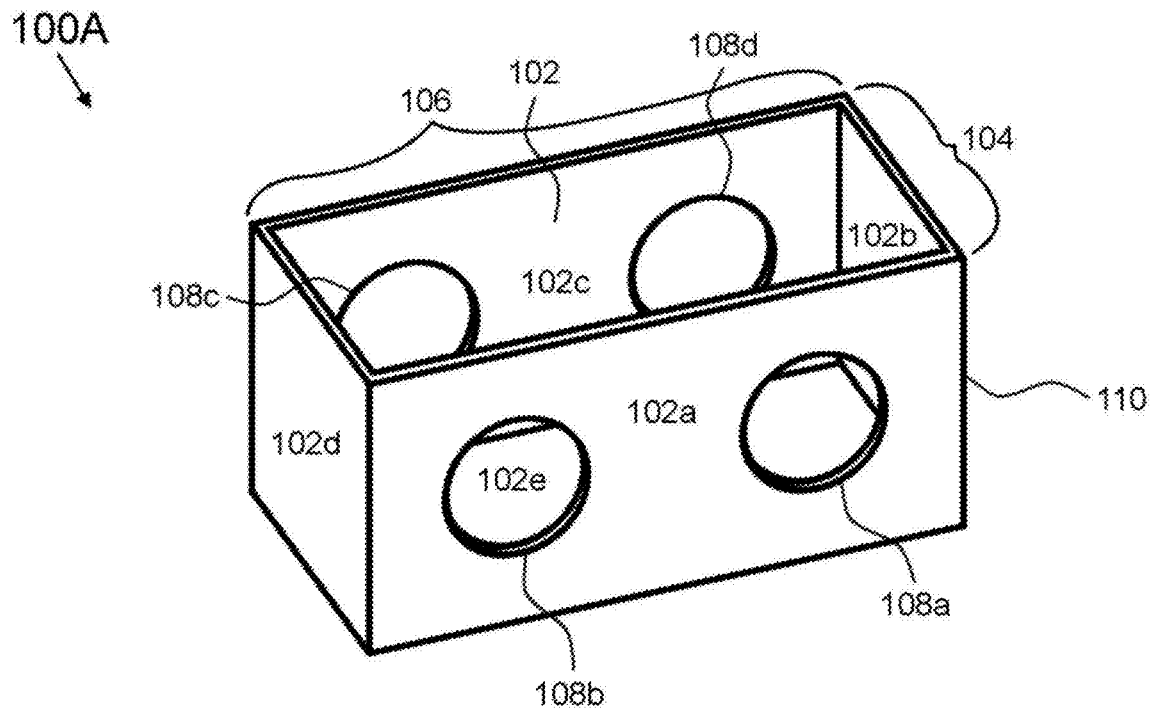
FIG. 1A
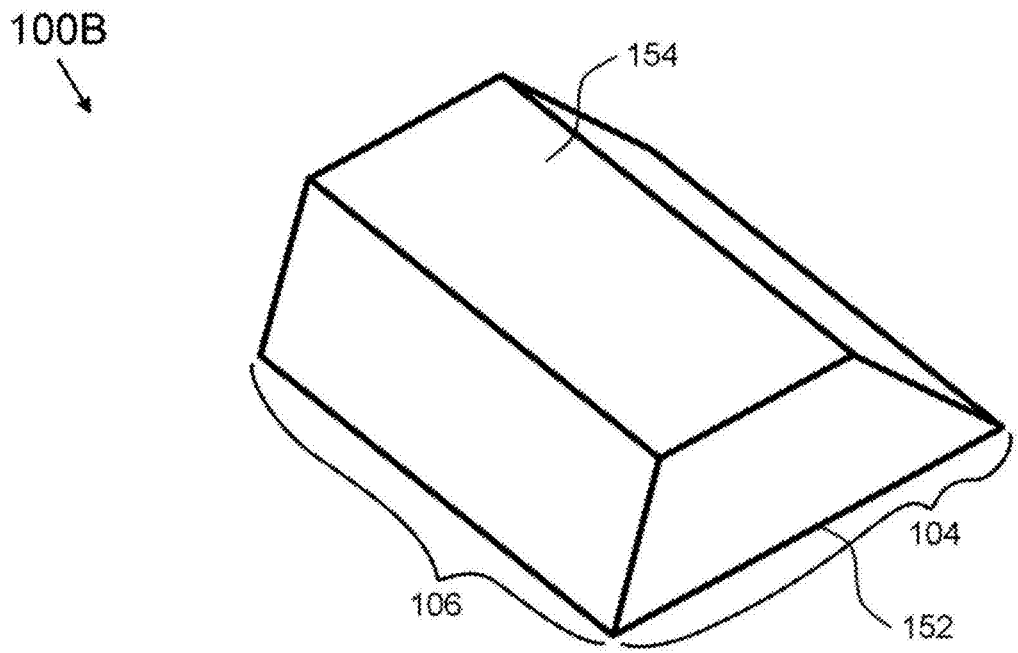
FIG. 1B
FIGS. 1A-1B

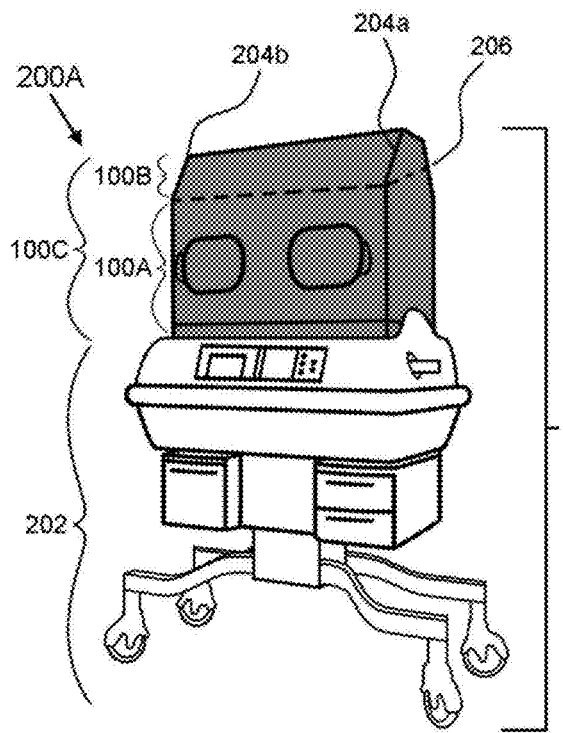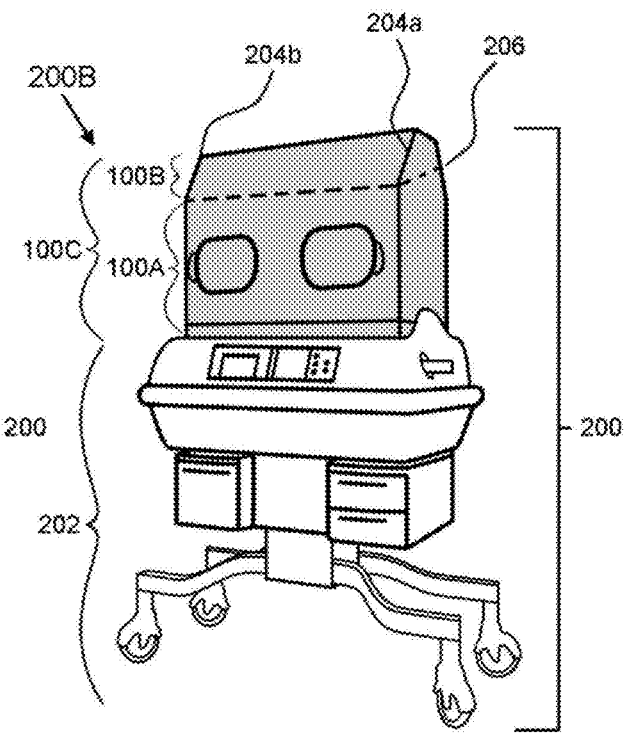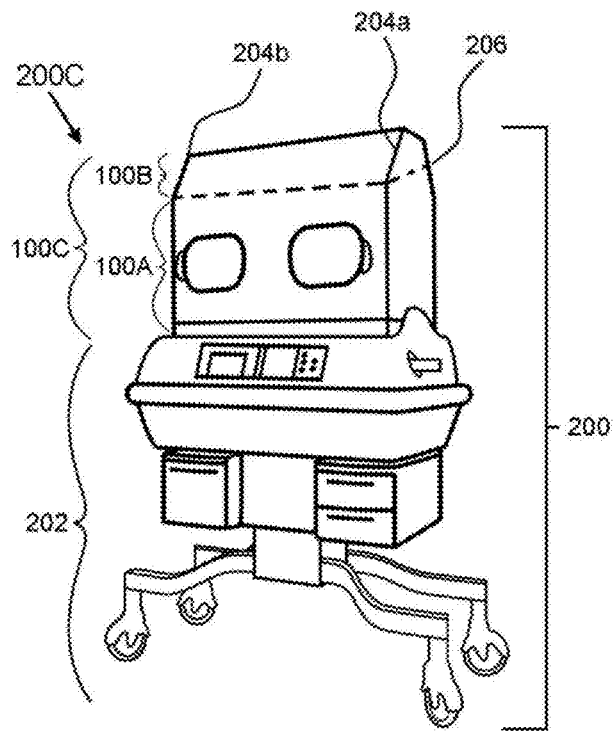
FIGS. 2A-C

FIGS. 3A-B

SYSTEMS AND METHODS FOR CONTROLLING LIGHT IN AN INCUBATOR

CROSS REFERENCE TO RELATED APPLICATIONS

This application claims priority under 35 U.S.C. § 119 to U.S. Provisional Application No. 62/627,444, entitled "Darkening of Pediatric Isolette Walls," and filed on Feb. 7, 2018. The contents of that application are hereby incorporated by reference in their entirety.

FIELD

The present disclosure relates to systems and methods for restricting light into an enclosed area.

BACKGROUND

Incubators are used for premature infants to control various parameters of the infants' environment, including temperature, humidity, and oxygen saturation. These parameters particularly require precise regulation in the neonatal intensive care unit (NICU) environment because premature neonates have underdeveloped organs and immune systems. Although incubators control several parameters, conventional incubators do not currently control light stimulus. NICUs typically have constant light stimulus provided by artificial overhead fluorescents; this constant light can interfere with the infants' sleep schedule and circadian rhythm development. Interference with an infant's sleep schedule causes cascading developmental delays, including: (1) neurodevelopment delays affecting visual recognition and memory, (2) development of photoreceptors, (3) abnormal brain development, (4) increased risk for respiratory and heart disease, (5) predisposition to internal cancer, (6) disturbances in neuroendocrine physiology development, and (7) inability to properly develop a circadian rhythm. Failure to develop a proper circadian rhythm impacts an infant's ability to regulate their: (1) sleep-wake cycle, (2) hormone release, (3) temperature, and (4) other various body functions.

Caretakers in conventional NICUs try to control the amount of light that is passed through the incubator by placing a blanket over the incubator. However, the constant darkness provided by these blankets can hinder the optical development of infants' eyes because no light stimulus is received. Additionally, the constant darkness can interfere with an infant's circadian rhythm, which can be detrimental to the infant's health.

Further, the conventionally-used blankets can be commercially produced or homemade, and are therefore associated with a high-degree of sanitation risk. There is no standard regulation behind the usage of the covers. For example, the covers can be placed back on the incubator immediately even they fall on the floor. These covers can fester bacteria, hold dust, and generally expose the infant to risk of infection. This sanitation risk is especially dangerous for premature infants, who generally have underdeveloped immune systems.

Furthermore, NICUs typically have many incubators—often dozens of units—in a single room. Each incubator can sound an alarm based on vitals of the infants inside the incubator. Conventional incubator covers can lead to delayed caretaker response times when an alarm goes off, because these covers prevent caretakers from readily identifying: (1) which incubator sounded the alarm; and (2) whether the infant inside the incubator actually requires attention. Additionally, the covers require manual action from the caretakers to remove them before checking the condition of the infant—thereby delaying the response time.

Furthermore, conventional covers increase the risk that a caretaker may not take proper notice of alarms. NICUs have numerous alarms every day, some of which may be false alarms. As result, these unnecessary alarms can desensitize the nurses. Covers increase the risk that a nurse might ignore an alarm because the nurse does not have a visual line of sight to the infant to determine whether assistance is actually needed.

Lastly, these conventional covers can pose fire-risks as they can be made of flammable material.

Altogether, conventional means of restricting the light stimulus to an infant in an incubator exposes the infant to numerous additional risks. Therefore, what is needed are systems and methods for restricting light stimulus to an infant in an incubator without exposing the infant to these additional risks.

SUMMARY

A first embodiment of the present disclosure provides for an incubator. The incubator can contain a premature human baby, or any other mammal requiring a controlled environment. The incubator can have a film, which has at least two configurations. In a first configuration, the film can be opaque to the transmission of light through the film; and in the second configuration, the film can be transparent to the transmission of light through the film.

In some examples, the film can include a third configuration, which has an intermediate optical property between opaqueness of the first configuration and transparency of the second configuration.

In some examples, the film can become transparent to the transmission of light through the film by applying an electric current to the film. This electric current can cause the second configuration.

In some examples, the film can include a colored dye. For example, the light within the incubator can then simulate light as seen from inside a womb.

In some examples, the incubator can include at least two sections of the film. Each section can be independently connected to a source of electric current. For example, mechanical fasteners can connect the sections of film to each other.

In some examples, a source of the electric current can initiate the electric current in response to an alarm. The alarm can be triggered by a monitor of a baby's physical condition.

In some examples, the film can be adhered to a transparent substrate.

In some examples, the incubator can include a central processing unit (CPU) and a circuit. The CPU and the circuit can control the application of the electric current to the film.

A second embodiment of the present disclosure can provide a method of caring for a premature human baby in an environment normally lit by natural or artificial light. The method can provide an incubator, according to the first embodiment. The method can then provide for increasing the exposure of the infant to light in the environment by intermittently energizing the film with an electric current. The electric current can cause the film to change to the second configuration, and be transparent to light or to a condition intermediate the first and the second configurations.

In some examples, the intermittent energizing of the film can be caused by a microprocessor and circuit. The microprocessor and circuit can be programmed to control the electrical energization of the film. In some examples, this programming can cause the energizing to regulate the circadian rhythm of the premature human baby.

In some examples, the intermittent energization of the film can be controlled by a caretaker of the premature human baby.

Additional examples of the second embodiment can be as provided above in the first embodiment.

A third embodiment of the present disclosure can provide for a method of eliminating ambient light from a portion of a workspace. The workspace can be normally lit by natural or artificial light. The method can provide for covering a portion of the workspace with a device. The device can have at least two configurations. In a first configuration, the device can be opaque to the transmission of light through the device; and in the second configuration, the device can be transparent to the transmission of light through the device.

In some examples, the device can include any of: (1) a film of polymer-dispersed liquid crystals; (2) suspended particles in a liquid suspension or film, (3) polarizing filters, (4) an electrically-controlled shutter system, and (5) an electrochromic device.

In some examples, the device can transition to the second configuration by applying an electric current or heat to the device. The electric current or heat can be applied in response to input from at least one sensor, for example. In other examples, the electric current can be applied in response to an input mechanism. The input mechanism can receive user input, such as for example, input from a caretaker. In some examples, the electric current or heat can be applied to less than all of the device, to change portions of the device to the second configuration.

In some examples, the workspace can be an incubator for containing a premature human baby, a mammal, or any other user requiring a controlled embodiment. Alternatively, it can be used where light sensitive materials need to be present, but ambient light exposure needs to be limited, such as when working with photosensitive chemicals or light initiated reactants, as in laboratories.

Additional examples of the third embodiment can be as provided for above with respect to the first and second embodiment.

For the purposes of the present disclosure, "incubator" refers to an enclosed apparatus which provides a controlled environment for the care and protection of an infant. The infant can be premature or unusually small. In some examples of the present disclosure, incubators can be used for non-human offspring. Incubators can provide controlled temperature, humidity, and oxygen levels. For the purposes of the present disclosure, "incubator" and "isolette" are used interchangeably.

In the present disclosure, "opacity" refers to the degree of opaqueness characterizing a material. For example, a material with a high degree of opacity is mostly (or entirely) opaque. A material with a low degree of opacity, by contrast, is mostly (or entirely) transparent.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A shows an exemplary base portion of an incubator cover, according to an embodiment of the present disclosure.

FIG. 1B shows an exemplary top portion of an incubator cover, according to an embodiment of the present disclosure.

FIGS. 2A-2C show various configurations of an exemplary incubator cover, according to various embodiments of the present disclosure.

DETAILED DESCRIPTION

Figure 1C:
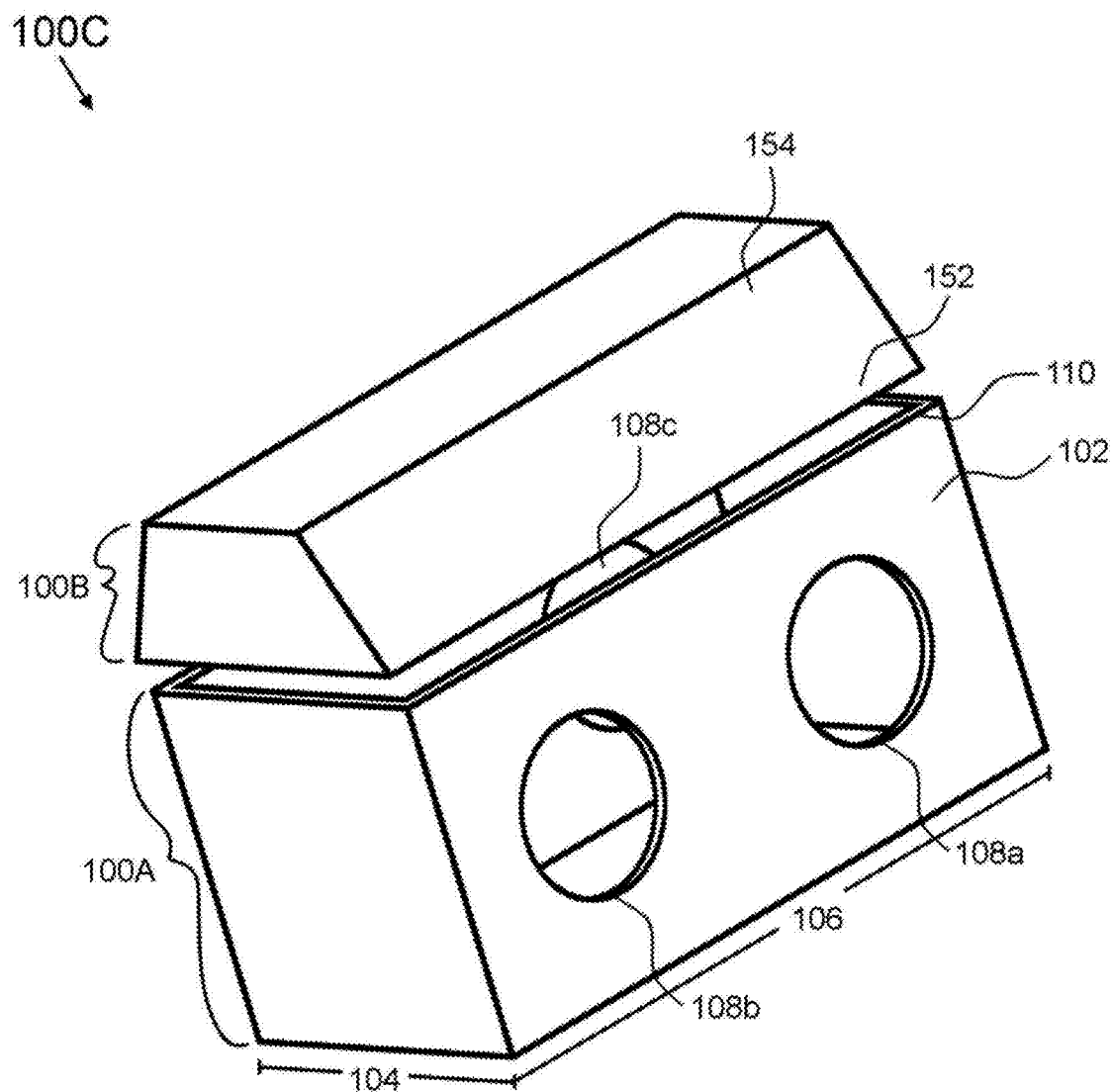
FIG. 1C shows an exemplary incubator cover formed by combining the base portion of FIG. 1A and the top portion of FIG. 1B, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure provides for an incubator system which includes a film covering the incubator housing. The film can have a plurality of configurations, including a first configuration to block the transmission of light through the film, and a second configuration to be transparent to the transmission of light. The film can further allow any number of additional configurations with varying degrees of opacity, with each opacity in between the opacities of the first and second configurations. The film can automatically change opacities based on input from an incubator processor or external devices configured to communicate with the incubator processor.

Therefore, the disclosed incubator system can provide controlled light cycling for infants, without incurring the risks of having a physical blanket covering the incubator. The disclosed incubator system can automatically adjust the opacity of the film, for example, to mirror natural circadian rhythms or to mimic the light environment of the womb. The disclosed incubator system can also immediately cause the film to become transparent if an alarm on the incubator is triggered. This allows the caretakers to instantly identify which infant needs attention, and quickly identify whether the alarm was necessary. Additional, non-limiting benefits and characteristics of the disclosed incubator system are discussed further below.

FIGS. 1A-1C show an exemplary housing with a bottom portion 100A and a top portion 100B. Although a particular shape bottom portion 100A and top portion 100B is shown in FIGS. 1A-1C, any shape and sizing can be provided for, so long as the shape and sizing can receive an infant. FIG. 1C shows an exemplary housing 100C, which can include a base housing 102; a width 104; a length 106; a plurality of openings 108a, 108b, 108c, 108d; a top edge 110 of the base housing 102; a top housing 154; a bottom edge 152 of the top housing 154; bottom portion 100A; and top portion 100B. FIG. 1A shows an isolated view of bottom portion 100A, and FIG. 1B shows an isolated view of top portion 100B. Although the present disclosure discusses the housing 100C with respect to an incubator, the housing 100C can be used for any workspace where systems and methods are needed to control the amount of light into a designated area.

FIG. 1A shows the bottom portion 100A, which has the base housing 102. The base housing 102 can have a width 104 and a length 106, which can be sized according to any conventional incubator sizing for housing an infant. The base housing 102 can further include a plurality of openings 108a, 108b, 108c, and 108d on base housing sides 102a and 102c. These openings 108a, 108b, 108c, and 108d can allow users to access an interior of the base housing 102, and can be sized appropriately for a user's arms. Although four openings 108a, 108b, 108c, and 108d are shown, any number of openings can be provided for, and can be located on any of the sides 102a, 102b, 102c, and 102d of the base housing 102—so long as the openings are not on the bottom 102e of the base housing 102. The openings 108a, 108b, 108c, and 108d can include doors (not pictured) which allow selective access to the interior of the base housing 102. Said doors can allow the base housing 102 to remain a controlled environment when the openings 108a, 108b, 108c, and 108d are not accessed.

Bottom portion 100A can be made primarily of glass or plastic, and can have a film covering the entire exterior of the base housing 100A. The film can cause an opacity of the base housing 100A to change (as discussed further with respect to FIGS. 3A-3B).

Referring now to FIG. 1B, top portion 100B can include a top housing 154 with a width 104 and length 106 to match the sizing of the bottom portion 100A. FIG. 1C shows how top edge 110 of 100A can be configured to receive bottom edge 152 of top portion 100B.

In some examples of the present disclosure, top edge 110 can mechanically couple with bottom edge 152, for example, via ridges, mechanical couplers, hinges, or any other means of coupling two housings together. Top portion 100B can be lifted to allow an infant to be put into and/or removed from apparatus 100C. In some examples, a section of top portion 100B can slide open to allow access to an interior of apparatus 100C.

In other examples of the present disclosure, bottom portion 100A and top portion 100B can be connected via a temporary or permanent seal. Such a seal can be airtight to ensure an environment within apparatus 100C can be isolated from an exterior of apparatus 100C.

FIGS. 2A-2C show various configurations 200A, 200B, and 200C of an exemplary incubator 200, according to various embodiments of the present disclosure. FIG. 2A shows a first configuration 200A of apparatus 100C, where apparatus 100C is completely opaque to the transmission of light; FIG. 2B shows an intermediate configuration 200B, where apparatus 100C is partially opaque to the transmission of light; and FIG. 2C shows a second configuration 200C, where apparatus 100C is completely transparent to the transmission of light. Incubator 200 can include the bottom housing 100A and top housing 100B of FIGS. 1A-1C. Incubator 200 can additionally include an incubator base 202, vertical edges 204a and 204b, and horizontal edge 206.

The incubator base 202 can be any apparatus designed to maintain particular environmental conditions in apparatus 100C. The incubator base 202 can be any incubator as known in the art, and can, in particular, control oxygen levels, temperature, and humidity. The incubator base 202 can also provide nutrition, medications, and fluid to an infant housed within the apparatus 100C. The incubator base 202 can be configured to receive sensor data, including data related to a state of the infant. The incubator base 202 can be further configured to provide an alarm based on the sensor data.

In some examples of the present disclosure, a film (as discussed with respect to FIGS. 3A-3B) can be applied to the surfaces of apparatus 100C. In some examples, this film can be permanently coupled to the surfaces of apparatus 100C (e.g., by a transparent substrate).

In other examples, the film, shutters, or other light-restricting mechanism can be removably coupled to apparatus 100C by mechanical fasteners. Exemplary mechanical fasteners can connect portions of the film to each other along edges 204a, 204b, and 206 of the apparatus 100C. These mechanical fasteners can include hook and loop fasteners, zippers, lip and tape fasteners, double track fasteners, and any combination thereof. These mechanical fasteners can provide a quick release function, so that the film can be quickly removed from the apparatus 100C to allow ease of access to the interior of apparatus 100C.

Figure 3A:
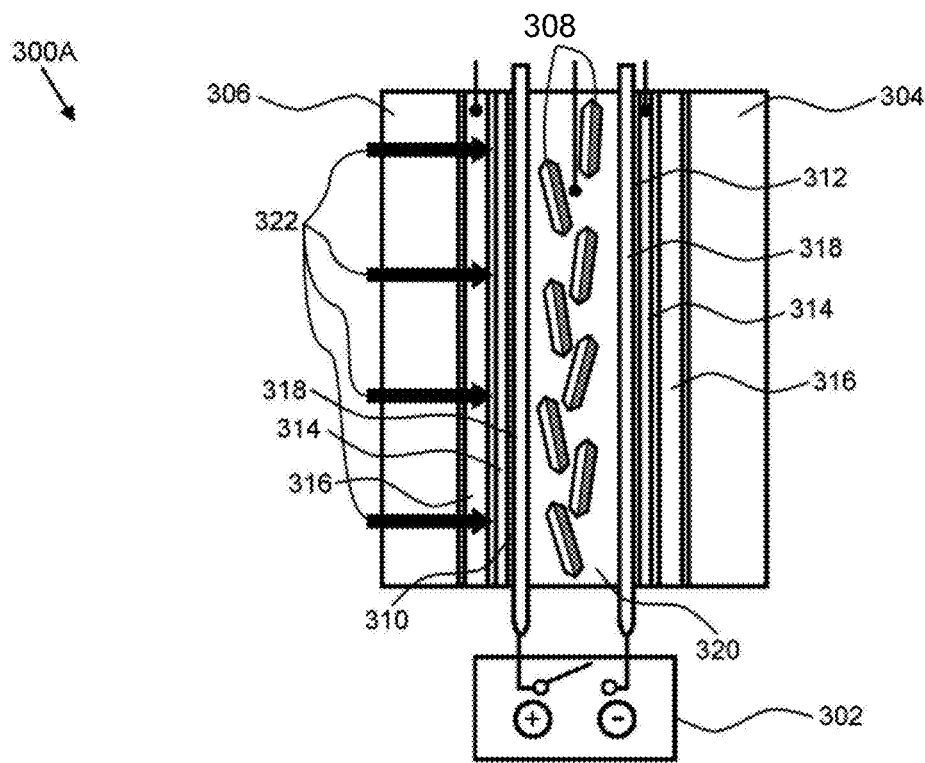
FIG. 3A shows an exemplary configuration of film when no electric current is applied, according to an embodiment of the present disclosure.
Figure 3B:
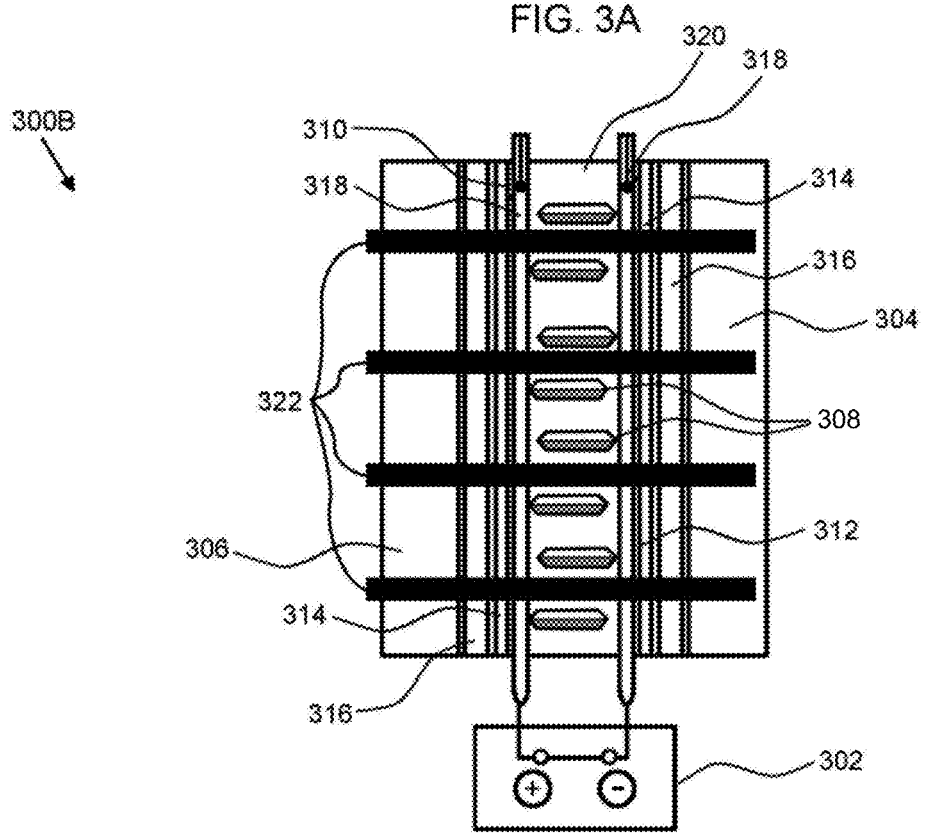
FIG. 3B shows an exemplary configuration of film when an electric current is applied, according to an embodiment of the present disclosure.

Apparatus 100C can transition between the various configurations as electric current is applied to the film (discussed further with respect to FIGS. 3A-3B). Although only one intermediate configuration 200B is shown, the disclosed incubator can provide for any number of intermediate configurations. Each intermediate configuration can have a different opacity from the other intermediate configurations. Furthermore, each intermediate configuration can have an opacity between a completely transparent configuration (configuration 200C) and a completely opaque configuration (configuration 200A).

Additionally, although FIGS. 2A-2C show the entire apparatus 100C transitioning between the configurations 200A, 200B, and 200C, some embodiments of the present disclosure provide for only particular portions of the apparatus 100C transitioning to different configurations. For example, the base portion 100A can remain opaque in the first configuration 200A, while the top portion 100B can transition to the second configuration 200C. In some examples, only particular faces of apparatus 100C can transition to different configurations. These independent transitions can be provided for by independently connecting different sections of apparatus 100C to a source of electric current.

FIGS. 3A-3B show various exemplary configurations 300A and 300B of a film, according to embodiments of the present disclosure. The film can include an electric current source 302, a first wall of glass 304, a second wall of glass 306, a plurality of molecules 308, a first side 310, a second side 312, a liquid film crystal 314, an interlayer film 316, a conductive coating 318, a liquid crystal layer 320, and external light 322.

The electric current source 302 can be a battery, an electrical outlet, an external generator, or any other device configured to output an electric current. The electric current source 302 can apply an electric current to the conductive coatings 318, which extend along parallel edges 310 and 312 of the liquid crystal layer 320. Conductive coatings 318 can be configured to generate a voltage difference between edges 310 and 312 in response to the generated electric current. The liquid crystal layer 320 can include a plurality of molecules 308. The molecules 308 can be randomly organized when no voltage is applied to the conductive coatings 318. The interlayer film 316 can be applied to glass 304 and 306, by a transparent material to form an air-tight seal between the film 316 and glass 304 and 306 (glass 304 can be glass sides 102a, 102b, 102c, and 102d of the apparatus 100C, for example).

FIG. 3A shows an opaque configuration 300A, where no voltage is applied to the conductive coatings 318. In configuration 300B, the molecules 308 are randomly organized, and this random organization can block external light 322 from passing between the two sides of glass 304 and 306. Configuration 300A can provide for configuration 200A of FIG. 2A.

FIG. 3B shows a transparent configuration 300B, where voltage is applied to the conductive coatings 318. In configuration 300B, the molecules 308 align in response to the applied voltage. The synchronous orientation of molecules 308 can allow external light 322 to pass between the two sides of glass 304 and 306, rendering film 300B completely transparent. Configuration 300A can provide for configuration 200C of FIG. 2C.

In some examples of the present disclosure, any of the glass 304 and 306, the liquid film crystal 314, the interlayer film 316, the conductive coating 318, and the liquid crystal layer 320 can include a colored dye. The colored dye can cause the external light 322 to appear a particular shade when viewed from within an apparatus covered by a film, as described with respect to FIGS. 3A-3B. For example, the colored dye can mimic the coloring of a womb.

In some examples of the present disclosure, film 300 can include any of: polymer dispersed liquid crystals; suspended particles in a liquid suspension or film; an electrochromic device; a photochromic device, which darkens with exposure to sunlight; a thermochromic device, which darkens in response to temperature change; a microblind, which changes opacity via electrodes curling based on electrostatic forces; layers of polarizing filters that can be rotated to prevent light transmittance; an electrically-controlled shutter system; and any combination thereof.

Figure 4:
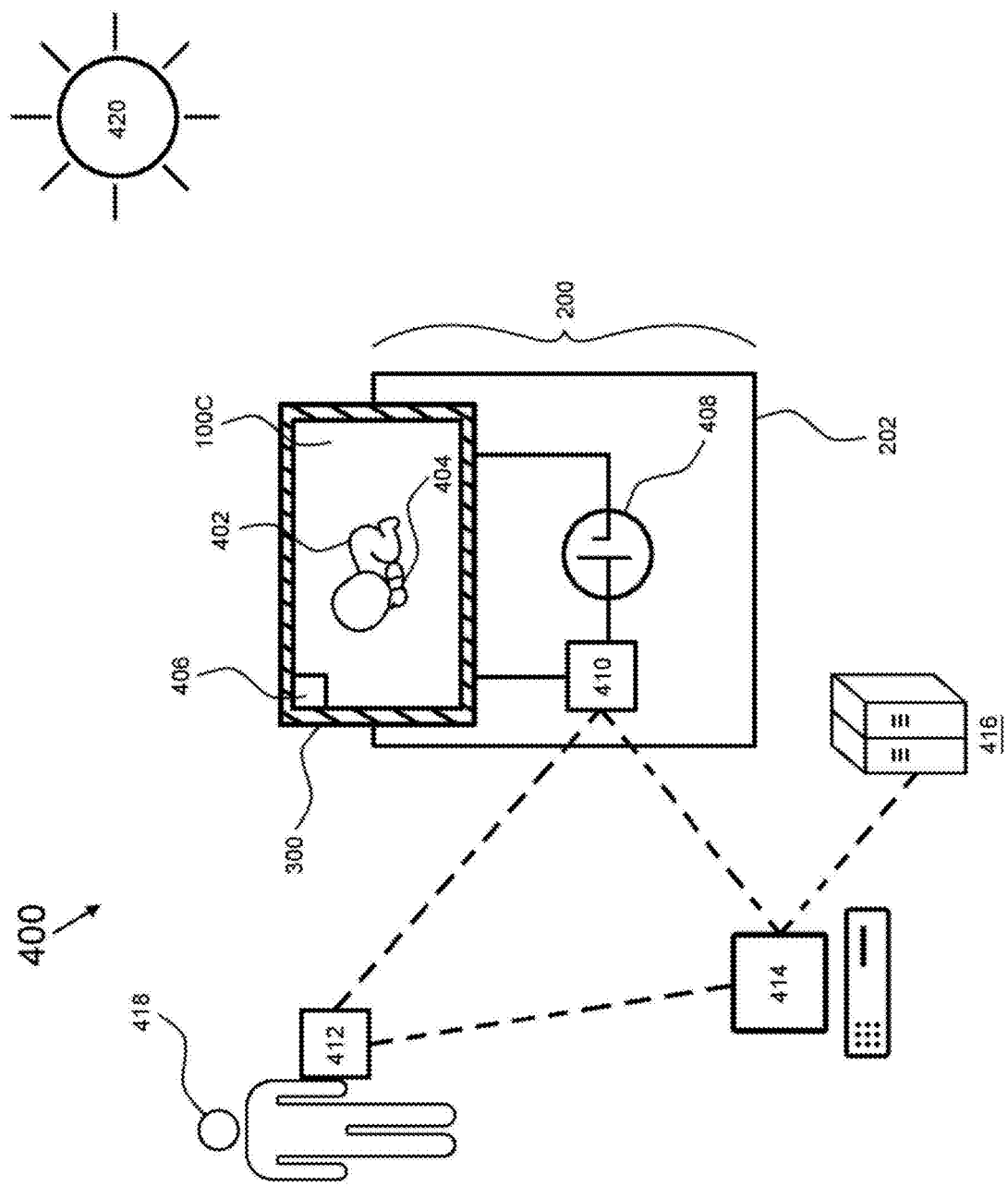
FIG. 4 shows an exemplary incubator system, according to an embodiment of the present disclosure.

FIG. 4 shows an exemplary incubator system 400, according to an embodiment of the present disclosure. System 400 can provide an exemplary system configured to control an opacity of an apparatus 100C based on various inputs. In system 400, apparatus 100C can be covered by films 300A and 300B, as discussed with respect to FIGS. 3A and 3C.

System 400 can include apparatus 100C of FIGS. 1A-1C, incubator base 202 of FIGS. 2A-2C, and a film 300 covering the apparatus 100C, as discussed with respect to FIGS. 3A-3B. System 400 can further include an infant 402, a physiological sensor 404, an external sensor 406, an electric current source 408, a processor 410, an input mechanism 412, an external computing device 414, an external memory 416, and a caretaker 418.

Apparatus 100C can be configured to contain an infant 402 in a controlled environment. Infant 402 can have at least one physiological sensor 404 connected to the infant to measure biological data. Physiological sensors 404 can include at least one or any combination of: a heart rate monitor, a blood flow sensor, a sweat sensor, a respiratory rate monitor, a pressure sensor, a blood pressure monitor, a blood glucose level sensor, an electrocardiogram sensor, a skin conductance sensor, and any other sensor known in the art. This physiological sensor 404 can be configured to communicate the collected data to a processor 410. System 400 can further include an external sensor 404, which can include any of a camera, a video recording device, a temperature sensor, a microphone, a humidity sensor, and any other sensor as conventionally known in the art. External sensor 406 can record data related to interior conditions of apparatus 100C, and can be communicatively coupled with the processor 410.

The processor 410 can be configured to receive data from the physiological sensor 404 and the external sensor 406. The processor 410 can adjust a variety of outputs of the incubator 200 based on the received data. For example, the processor 410 can adjust temperature, humidity, and oxygen levels inside apparatus 100C. The processor can also be communicatively coupled to an input mechanism 412 and an external computing device 414. In some examples, the processor 410 can initiate an alarm based on input received from the sensors 404 and 406. An exemplary alarm can alert caretaker 418 to a condition of the infant 402, especially when the infant 402 requires immediate medical attention.

Additionally, based on the input from sensors 404 and 406, the processor 410 can adjust an amount of electric current provided by the electric current source 408 to the film 300. The electric current source 408 can be as provided for with respect to the electric current source 302 of FIGS. 3A-3B. Therefore, adjusting the electric current applied to the film can vary the level of opacity of the apparatus 100C.

For example, external sensor 406 can sense external light 420, and can send the data to the processor 410, which adjusts an opacity of film 300 based on the received data. An infant 402 can require higher amounts light during the day, and lower amounts of light at night. In another example, the processor 410 can automatically cause one or more portions of apparatus 100C to become transparent based on input from sensors 404 and 406. This automatic adjustment of the opacity of apparatus 100C can coincide with an alarm, for example.

The input mechanism 412 can be controlled by a caretaker 418 (as shown in FIG. 4A) or physically attached to the incubator 200 (not pictured). The input mechanism 412 can be a switch, a smart phone app, a pager, a radio, or any other means of sending commands to the processor 410, as known in the art. The input mechanism 412 can adjust any controls of the incubator 200, and can further cause an opacity of the film 300 to change. For example, if caretaker 418 wants to check on infant 402, the caretaker 418 can cause one or more portions of film 300 to become transparent via the input mechanism 412.

The external computing device 414 can receive data from the processor 410, including data from sensors 404 and 406. The external computing device 414 can store sensor data in an external memory module 416. In some examples, the external computing device 414 or the processor 410 can store instructions, which causes the processor 410 to intermittently energize the film 300 to change between transparent and opaque configurations. In some examples, the processor 410 can adjust the opacity of the film 300 in order to regulate circadian rhythm of the infant 402.

In some additional examples of FIG. 4A, the external computing device 414 can store a medical history of infant 402 in memory modules 416. The external computing device 414 can determine whether vitals of infant 402 are out of a normal range, based on sensor data from sensors 404 and 406 and the stored medical history. The processor 410 can cause the film 300 to go completely clear if vitals are detected to be out of a normal range. In some examples, the external computing device 414 can use machine learning to determine when the vitals are outside of a normal range. Therefore, processor 410 and external computing device 414 can provide personal baselines for each infant.

In some examples, the processor 410 can cause film 300 to provide a unique pattern of transparency based on sensor data from sensors 404 and 406. For example, the unique pattern can indicate to a caretaker particular information about infant 402 (e.g., three quick, consecutive flashes can indicate that the infant's 402 nutrient supply is running low). Any pattern can be assigned to sensor data 404 and 406.

In some examples of the disclosed incubator, the processor 410 can be a central processing unit (CPU) and a circuit. Any microcontroller known in the art can be used for the processor 410, including at least one of: an Arduino, a Raspberry Pi, a LaunchPad, a Nanode, a pinguino, a STM32 Discovery, a NodeMCU, a teensy, and any other microcontroller, as known in the art.

Additionally, although various aspects of incubator functions are disclosed, any aspects of the incubator 200 can be adjusted in response to sensor data. These aspects can be any environmental controls or responses, as known in the art.

Alternative Embodiments

Although the disclosed incubator is discussed with respect to a film 300 applied to an exterior of the apparatus 100C, any light-restricting mechanism can be used, so long as the chosen light-restricting mechanism can increase and decrease light stimulus to an interior of the incubator. For example, shutters, curtains, or other mechanisms can be used. The shutters and curtains can be controlled by the microprocessor 410 of FIG. 4A, and can automatically open and close based on commands from the microprocessor 410.

Additionally, apparatus 100C with a layer of film 300, although primarily discussed as an apparatus designed to receive an infant, can be an apparatus designed to cover any portion of a workspace, which requires varying light stimulus. For example, apparatus 100C with film 300 can be configured to hold plants or fungi in order to control the amount of sunlight received by the plants. For example, such a configuration can help plants or fungi, which require minimal amounts of sunlight, to grow in environments which are naturally well-lit. In another example, the disclosed technology can be used as greenhouse windows or walls.

In another example, apparatus 100C with film 300 can be configured to fit over a crib or bed to help with the sleep cycle of a child (or even a grown person).

In another example, apparatus 100C can be large enough to be used in a livestock farm to establish circadian rhythm for the animals in the livestock farm.

Computer System

Figure 5:
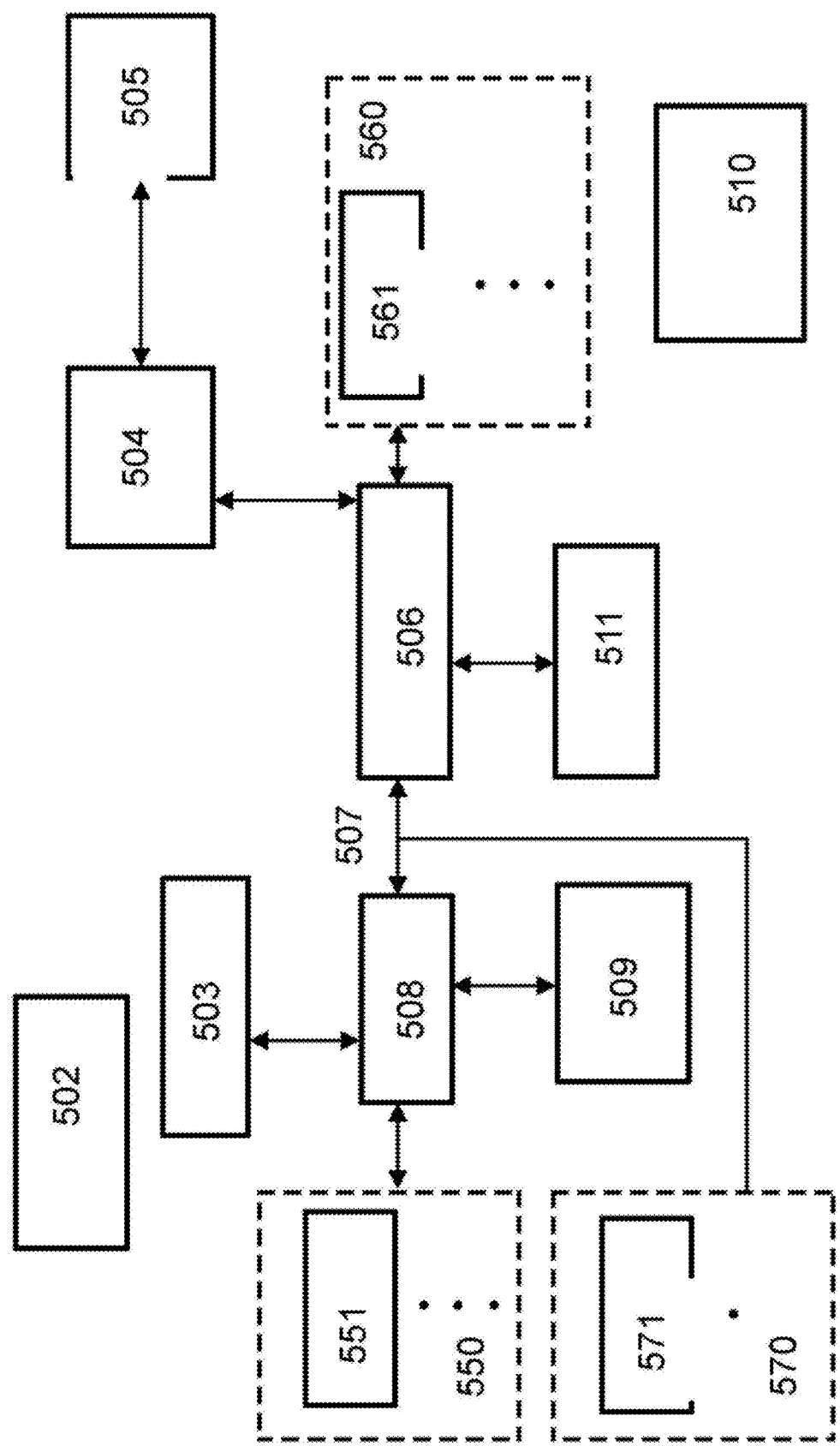
FIG. 5 is a schematic block diagram illustrating an exemplary system, in accordance with an implementation of the present disclosure.

FIG. 5 is a schematic block diagram illustrating an exemplary server system 500, in accordance with an implementation of the present disclosure. In this example, the server system 500 includes at least one microprocessor or processor 504; a BMC 503; one or more cooling modules 560; a main memory (MEM) 511; at least one power supply unit (PSU) 502 that receives an AC power from an AC power supply 501, and provides power to various components of the server system 500, such as the processor 504, north bridge (NB) logic 506, PCIe slots 560, south bridge (SB) logic 508, storage device 509, ISA slots 550, PCI slots 570, and/or BMC 503.

After being powered on, the server system 500 is configured to load software application from memory, a computer storage device, or an external storage device to perform various operations. The storage device 509 is structured into logical blocks that are available to an operating system and applications of the server system 500. The storage device 509 is configured to retain server data even when the server system 500 is powered off.

In FIG. 5, the memory 511 is coupled to the processor 504 via the NB logic 506. The memory 511 may include, but is not limited to, dynamic random access memory (DRAM), double data rate DRAM (DDR DRAM), static RAM (SRAM), or other types of suitable memory. The memory 511 can be configured to store firmware data of the server system 500. In some configurations, firmware data can be stored on the storage device 509.

In some implementations, the server system 500 can further comprise a flash storage device. The flash storage device can be a flash drive, a random access memory (RAM), a non-volatile random-access memory (NVRAM), or an electrically erasable programmable read-only memory (EEPROM). The flash storage device can be configured to store system configurations such as firmware data.

The processor 504 can be a central processing unit (CPU) configured to execute program instructions for specific functions. For example, during a booting process, the processor 504 can access firmware data stored in the BMC 503 or the flash storage device, and execute the BIOS 505 to initialize the server system 500. After the booting process, the processor 504 can execute an operating system in order to perform and manage specific tasks for the server system 500.

In some configurations, the processor 504 can be multi-core processors, each of which is coupled together through a CPU bus connected to the NB logic 506. In some configurations, the NB logic 506 can be integrated into the processor 504. The NB logic 506 can also be connected to a plurality of peripheral component interconnect express (PCIe) slots 560 and an SB logic 508 (optional). The plurality of PCIe slots 560 can be used for connections and buses such as PCI Express x1, USB 2.0, SMBus, SIM card, future extension for another PCIe lane, 1.5 V and 3.3 V power, and wires to diagnostics LEDs on the server system 500's chassis.

In system 500, the NB logic 506 and the SB logic 508 are connected by a peripheral component interconnect (PCI) Bus 507. The PCI Bus 507 can support functions on the processor 504 but in a standardized format that is independent of any of the processor 504's native buses. The PCI Bus 507 can be further connected to a plurality of PCI slots 570 (e.g., a PCI slot 571). Devices connect to the PCI Bus 507 may appear to a bus controller (not shown) to be connected directly to a CPU bus; assigned addresses in the processor 504's address space; and synchronized to a single bus clock. PCI cards that can be used in the plurality of PCI slots 570 include, but are not limited to, network interface cards (NICs), sound cards, modems, TV tuner cards, disk controllers, video cards, small computer system interface (SCSI) adapters, and/or personal computer memory card international association (PCMCIA) cards.

The SB logic 508 can couple the PCI Bus 507 to a plurality of expansion cards or ISA slots 550 (e.g., an ISA slot 551) via an expansion bus. The expansion bus can be a bus used for communications between the SB logic 508 and peripheral devices, and may include, but is not limited to, an industry standard architecture (ISA) bus, PC/504 bus, low pin count bus, extended ISA (EISA) bus, universal serial bus (USB), integrated drive electronics (IDE) bus, or any other suitable bus that can be used for data communications for peripheral devices.

In this example, BIOS 505 can be any program instructions or firmware configured to initiate and identify various components of the server system 500. The BIOS is an important system component that is responsible for initializing and testing hardware components of a corresponding server system. The BIOS can provide an abstraction layer for the hardware components, thereby providing a consistent way for applications and operating systems to interact with a peripheral device such as a keyboard, a display, and other input/output devices.

In system 500, the SB logic 508 is further coupled to the BMC 503 that is connected to the PSU 502. In some implementations, the BMC 503 can also be a rack management controller (RMC). The BMC 503 is configured to monitor operation status of components of the server system 500, and control the server system 500 based upon the operation status of the components.

Although only certain components are shown within the exemplary systems 500 in FIG. 5, various types of electronic or computing components that are capable of processing or storing data, or receiving or transmitting signals, can also be included in the exemplary system 500. Further, the electronic or computing components in the exemplary system 500 can be configured to execute various types of application, and/or can use various types of operating systems. These operating systems can include, but are not limited to, Android, Berkeley Software Distribution (BSD), iPhone OS (iOS), Linux, OS X, Unix-like Real-time Operating System (e.g., QNX), Microsoft Windows, Window Phone, and IBM z/OS.

Depending on the desired implementation for the exemplary systems 500, a variety of networking and messaging protocols can be used, including but not limited to TCP/IP, open systems interconnection (OSI), file transfer protocol (FTP), universal plug and play (UpnP), network file system (NFS), common internet file system (CIFS), AppleTalk etc. As would be appreciated by those skilled in the art, FIG. 5 is used for purposes of explanation. Therefore, a network system can be implemented with many variations, as appropriate, yet still provide a configuration of network platform in accordance with various examples of the present disclosure.

In exemplary configurations of FIG. 5, the exemplary system 500 can also include one or more wireless components operable to communicate with one or more electronic devices within a computing range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections, as known in the art. Various other elements and/or combinations are possible as well within the scope of various examples.

While various examples of the present invention have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. An incubator system for containing a premature baby, comprising:
    an incubator comprising a film, the film being opaque to the transmission of light through the film in a first configuration, and transparent to the transmission of light in a second configuration;
    at least one physiological sensor within the incubator, said at least one physiological sensor configured to receive data from the premature baby within the incubator;
    wherein the at least one physiological sensor is one selected from the group consisting of a heart rate monitor, a blood flow sensor, a sweat sensor, a respiratory rate sensor, a blood pressure monitor, a blood glucose level sensor, an electrocardiogram sensor, a skin conductance sensor, and combinations thereof;
    wherein the film alternates between the first configuration and the second configuration based on the data received from the at least one physiological sensor.

2. The incubator system of claim 1, wherein the film becomes transparent to the transmission of light in the second configuration by applying an electric current to the film.

3. The incubator system of claim 2, wherein the incubator comprises at least two sections of the film; each section of the film being independently connected to a source of electric current.

4. The incubator system of claim 3, further comprising a mechanical fastener to connect the at least two sections of film to each other.

5. The incubator system of claim 4, wherein the fastener is at least one selected from the group consisting of a hook and loop fastener, a zipper, a lip and tape fastener, a double track fastener, and any combination thereof.

6. The incubator system of claim 2, further comprising a central processing unit (CPU) and circuit to control the application of the electric current to the film.

7. The incubator system of claim 6, wherein the central processing unit (CPU) and circuit are also connected to the at least one physiological sensor.

8. The incubator system of claim 6, wherein the central processing unit and circuit are also connected to an external sensor.

9. The incubator system of claim 8, wherein the external sensor is one selected from the group consisting of a camera, a video recording device, a humidity sensor, and combinations thereof.

10. The incubator system of claim 8, wherein the external sensor is a camera.

11. The incubator system of claim 1, wherein the film comprises at least one additional configuration, the at least one additional configuration having an intermediate opacity between opaqueness of the film in the first configuration and the transparency of the film in the second configurations.

12. The incubator system of claim 1, wherein the film comprises a colored dye.

13. The incubator system of claim 1, further comprising a processor wherein the data from the at least one physiological sensor can initiate an alarm when the source of electric current is applied to create the second configuration of the film.

14. The incubator system of claim 1, wherein the film is adhered to a transparent substrate.

15. The incubator system of claim 1, wherein the at least one physiological sensor is one selected from the group consisting of a heart rate monitor, a blood flow sensor, a respiratory rate sensor, a blood pressure monitor, a blood glucose level sensor, an electrocardiogram sensor, and combinations thereof.

16. A method of caring for a premature baby in an environment normally lit by natural or artificial light, the method comprising:
   providing an incubator system according to claim 1;
   wherein the film in the first configuration is opaque to transmission of light when no electric current is applied to the film; and
   increasing the exposure of the premature baby to light in the environment by intermittently energizing the film with an electric current to change the film to the second configuration in response to data received from the at least one physiological sensor.

17. The method of claim 16, wherein the intermittent energizing of the film comprises providing a microprocessor and circuit programmable to control the electrical energization of the film to regulate circadian rhythm of the premature baby based on the data received from the at least one physiological sensor.

18. The method of claim 16, wherein the intermittent energization of the film is also controlled by a caretaker of the premature baby.

19. An incubator system for containing a premature baby, comprising:
   an incubator comprising a film, the film being opaque to the transmission of light through the film in a first configuration, and transparent to the transmission of light in a second configuration when an electric current is applied to the film;
   at least one physiological sensor selected from the group consisting of a heart rate monitor, a blood flow sensor, a sweat sensor, a respiratory rate sensor, a blood pressure monitor, a blood glucose level sensor, an electrocardiogram sensor, a skin conductance sensor, and combinations thereof within the incubator, said at least one physiological sensor configured to receive data from the premature baby within the incubator;
   wherein the film changes to the second configuration by the application of electric current to the film based on the data received from the at least one physiological sensor.

20. The incubator system of claim 19, further comprising an alarm, the alarm being actuated in response to data received from the at least one physiological sensor, whereby actuation of the alarm coincides with the film changing to the second configuration.

* * * * *